United States Patent [19] [11] 4,036,986
Yamada et al. [45] July 19, 1977

[54] FUNGICIDAL N-(4-HALOBENZYL)-N-SEC. ALKYL-N'-PHENYLTHIOUREAS

[75] Inventors: Yasuo Yamada, Tokyo, Japan; Junichi Saito, Wuppertal, Germany; Tatsuo Tamura; Yoshio Kurahashi, both of Tokyo, Japan

[73] Assignee: Bayer Aktiengesellschaft, Leverkusen, Germany

[21] Appl. No.: 644,242

[22] Filed: Dec. 24, 1975

[30] Foreign Application Priority Data

Dec. 24, 1974  Japan ............................ 49-147526

[51] Int. Cl.$^2$ ............................................. A01N 9/12
[52] U.S. Cl. ................................. 424/322; 260/552 R
[58] Field of Search .................... 260/552 R; 424/322

[56] References Cited
U.S. PATENT DOCUMENTS 3,829,485   8/1974   Martin et al. .................... 260/552 R

FOREIGN PATENT DOCUMENTS 29,252   11/1969   Japan

Primary Examiner—Leonard Schenkman
Attorney, Agent, or Firm—Burgess, Dinklage & Sprung

[57] ABSTRACT

N-(4-halobenzyl)-N-sec. alkyl-N'-phenylthioureas of the formula

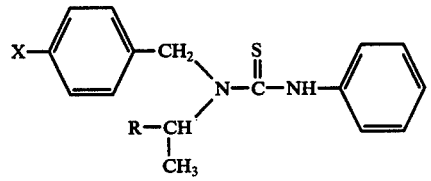

in which
R is a $C_1$–$C_6$ alkyl radical, and
X is a halogen atom.
which possess fungicidal properties.

10 Claims, No Drawings

FUNGICIDAL N-(4-HALOBENZYL)-N-SEC. ALKYL-N'-PHENYLTHIOUREAS

The present invention relates to and has for its objects the provision of particular new N-(4-halobenzyl)-N-sec. alkyl-N'-phenylthioureas, which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It is known from published Japanese Patent Application No. 29252/1969 that urea compounds having the general formula:

(VI)

[Structure VI: a diphenyl urea with substituents $R_1, R_2, R_3, R_4, R_5$ on one ring, $R_6, R_7, R_8, R_9, R_{10}$ on the other, linked by $R_{11}$—N($R_{12}$)—C(=X)—N($R_{13}$)—]

in which
X is an oxygen or sulfur atom,
$R_1, R_2, R_3, R_4, R_5, R_6, R_7, R_8, R_9$ and $R_{10}$, which may be the same or different, are each a hydrogen atom, a lower alkyl radical, a lower alkoxy radical or an —$NO_2$ radical, with the proviso that at least two of $R_1$–$R_5$ radicals and at least two of $R_6$–$R_{10}$ radicals are not hydrogen atoms,
$R_{11}$ is a straight-chain alkylene radical, and
$R_{12}$ and $R_{13}$ are each a hydrogen atom or a lower alkyl radical, have insecticidal, acaricidal, fungicidal and/or herbicidal activities.

At present, fungicidal agents which contain, as active ingredients, organic arsenic compounds are mainly used for the control of rice plant sheath blight. In addition, a few agents which contain antibiotics or organic phosphorus compounds are used.

However, the use of organic arsenic compounds is not desirable in view of their toxicity and in view of environmental considerations. Furthermore, other known fungicidal agents, which contain antibiotics or organic phosphorus compounds, do not exhibit sufficient fungicidal activity for a long period of time. Thus, there exists a need for a fungicidal agent which can be advantageously used, instead of the above-mentioned known agents, for the control of rice plant sheath blight.

The present invention now provides, as new compounds, the thiourea compounds having the general formula (I)

[Structure I: 4-X-phenyl-$CH_2$—N(CH(R)CH$_3$)—C(=S)—NH-phenyl]

in which

R is a $C_1$–$C_6$ alkyl radical, and
X is a halogen atom.

The compounds of the formula (I) have been found to exhibit a strong fungicidal activity, especially when compared to the active compounds disclosed in Japanese Patent Application No. 29252/1969, referred to above.

Preferably, R is a $C_1$–$C_4$ alkyl radical, namely methyl, ethyl, n- or isopropyl or n-, sec.-, iso- or tert.-butyl; X is fluorine, chlorine, bromine or iodine.

The present invention also provides a process for the preparation of a compound of the formula (I), in which
(a) an amine having the general formula (II),

[Structure II: 4-X-phenyl-$CH_2$—NH—CH(R)CH$_3$]

in which
R and X have the meanings stated above,
is reacted with phenyl isothiocyanate, having the formula (III),

[Structure III: S=C=N-phenyl]

or (b) a thiocarbamoyl chloride having the general formula (IV),

[Structure IV: 4-X-phenyl-$CH_2$—N(CH(R)CH$_3$)—C(=S)—Cl]

is reacted with aniline, having the formula (V).

[Structure V: $H_2$N-phenyl]

When N-[4-chlorobenzyl]-N-sec.-butyl-amine and phenyl isothiocyanate are used as starting materials in process variant (a), the reaction can be represented by the following equation:

[Reaction: 4-Cl-phenyl-$CH_2$—NH—CH(CH$_3$)CH$_2$CH$_3$ (IIa) + S=C=N-phenyl (III)]

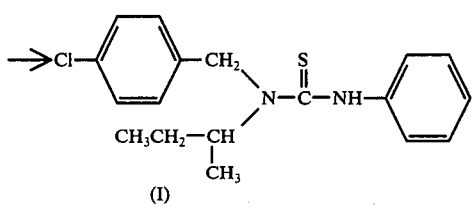

(I)

Examples of the amines of the formula (II), which can be used as starting materials in process variant (a) above, are as follows:

N-[4-fluoro-(or chloro- or bromo- or iodo-) benzyl]-N-isopropyl-amine,
N-[4-fluoro- (or chloro- or bromo- or iodo-)benzyl]-N-sec.-butyl-amine,
N-[4-fluoro- (or chloro- or bromo- or iodo-)benzyl]-N-(1-methylbutyl)-amine,
N-[4-fluoro- (or chloro- or bromo- or iodo-)benzyl]-N-(1,2-dimethylpropyl)-amine, and
N-[4-fluoro- (or chloro- or bromo- or iodo-)benzyl]-N-(1-methylpentyl)-amine.

The process variant (a) for producing the present active compounds is carried out preferably in the presence of a solvent or a diluent. As well as water, any inert organic solvent or diluent may be employed for this purpose, especially one selected from aliphatic and aromatic hydrocarbons which may optionally be chlorinated, for example hexane, cyclohexane, petroleum ether, ligroin, benzene, toluene, xylene, methylene chloride, chloroform, carbon tetrachloride, ethylene chloride, trichloroethylene or chlorobenzene; ethers, for instance diethyl ether, methyl ether, di-isopropyl ether, dibutyl ether, propylene oxide, dioxane or tetrahydrofuran; ketones, for instance acetone, methyl ethyl ketone, methyl isopropyl ketone or methyl isobutyl ketone; nitriles, for instance acetonitrile, propionitrile or acrylonitrile; esters, for instance ethyl acetate or amyl acetate; acid amides, for instance dimethylformamide or dimethylacetamide; sulfones and sulfoxides, for instance dimethyl sulfoxide or dimethyl sulfone; and bases, for instance pyridine.

The process variant (a) according to the present invention can be carried out over a wide temperature range. Generally, it is carried out at a temperature of from −20° C to the boiling point of the reaction mixture, preferably at from 0° to 100° C or to the boiling point of the reaction mixture, whichever is the lower.

The reaction is preferably carried out under an ambient pressure, but it can also be operated under elevated or reduced pressures.

If N-[4-chlorobenzyl]-N-isopropyl-thiocarbamoyl chloride and aniline are used as starting materials in process variant (b), the reaction can be represented by the following equation:

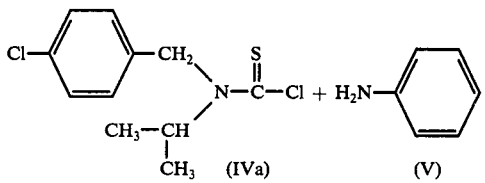

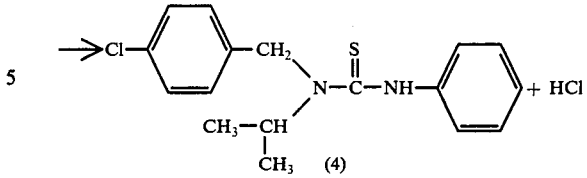

(4)

Examples of the thiocarbamoyl chlorides of the formula (IV), which can be employed in process variant (b) above, are as follows:

N-[4-fluoro- (or chloro- or bromo- or iodo-)benzyl]-N-isopropyl-thiocarbamoyl chloride,
N-[4-fluoro- (or chloro- or bromo- or iodo-)benzyl]-N-sec.-butyl-thiocarbamoyl chloride,
N-[4-fluoro- (or chloro- or bromo- or iodo-)benzyl]-N-(1-methylbutyl)-thiocarbamoyl chloride,
N-[4-fluoro- (or chloro- or bromo- or iodo-)benzyl]-N-(1,2-dimethylpropyl)-thiocarbamoyl chloride, and
N-[4-fluoro- (or chloro- or bromo- or iodo-)benzyl]-N-(1-methylpentyl)-thiocarbamoyl chloride.

When the present active compounds are prepared according to the process variant (b), it is preferred to use a solvent or diluent as mentioned above in the discussion of process variant (a).

The process variant (b) can be carried out in the presence of an acid-binding agent. Examples of such acid-binding agents are the conventional acid acceptors such as alkali metal hydroxides, carbonates, bicarbonates or alcoholates, and tertiary organic bases, for example triethylamine, dimethyl aniline and pyridine.

Process variant (b) can also be carried out over a wide range of temperatures. Generally, it is carried out at a temperature of from −20° C to the boiling point of the reaction mixture, preferably at from 0° to 50° C, or to the boiling point of the reaction mixture, whichever is the lower.

The reaction is preferably carried out under an ambient pressure but it can also be operated under elevated or reduced pressures.

The active compounds according to the invention exhibit a powerful fungitoxic action. The compounds according to the invention have only a low toxicity to warm-blooded animals. Moreover, they are well tolerated by plants, that is to say, they do not damage crop plants in the concentrations required for combating fungi. For this reason, they are suitable for use as plant protection agents for combating fungi. Fungitoxic agents are employed in plant protection for combating Archimycetes, Phycomycetes, Asocomycetes, Basidiomycetes and Fungi Imperfecti.

In particular, the active compounds are highly effective for the control of phytopathogenic species of Basidiomycetes, for instance, those causing sheath blight and seedling-rot diseases of rice plants.

The active compounds according to the invention have a broad spectrum of action and can be employed againt parasitic fungi which attach above-ground parts of plants or which attack the plants through the soil to cause tracheomycosis, and against seed-borne pathogens. They display a particularly good activity against fungi causing sheath blight (*Pellicularia sasakii*) and seedling rot (*Pellicularia filamentosa*), which are serious diseases of rice plants. In addition, the active compounds are effective for the control of the following diseases of crop plants: sclerotial blight (*Corticium centrifugum*), blast (*Pyricularia oryzae*), rice bacterial leaf blight (*Xanthomonas oryzae*), Chinese cabbage slimy soft rot (*Erwinia aroideae*), citrus canker (*Xanthomonas citri*), brown spot disease of rice (*Cochliobolus miyabeanus*), banana leaf spot (*Mycosphaerella musicola*), common gray mold (*Botrytis cinerea*), grape downy mildew (*Plasmopara viticola*), bitter rot of apples, grapes, and pears (*Glomella cingulata*), root rot or drop of lettuce (*Sclerotinia sclerotiorum*), anthracnose of cucumbers (*Colletotrichum lagenarium*), citrus melanose (*Diaporthe citri*), powdery mildew of apples (*Podospharea leucotricha*), cucumber powdery mildew (*Sphaerotheca fuliginea*), black spot, such as apple leaf spot (*Alternaria mali*), potato early blight (*Alternaria solani*) and pear black spot (*Alternaria kikuchiana*), and scab, such as apple scab (*Venturia inaequalis*) and pear scab (*Venturia pirina*).

Owing to the excellent fungicidal properties mentioned above, the active compounds according to the present invention can also be employed with advantageous results against diseases caused by phytopathogenic fungi which hitherto had to be controlled by fungicides containing such heavy metals as arsenic or mercury, which are deleterious to human beings and domestic animals.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl aryl polyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides, or insecticides, acaricides, nematocides, bactericides, rodenticides, herbicides, fertilizers, growth-regulating agents, nutrients, antibiotics, antiviral agents, etc., if desired, or in the form of particular dosage preparations for specific application made therefrom, such as solutions, emulsions, suspensions, powders, pastes, granules, very fine capsules in polymeric substances and in coating composition suited for use on seed, and fumigating cartridges.

As concerns commercially marketed preparations, these generally contemplate carrier composition mixtures in which the active compound is present in an amount substantially between about 0.1-95% by weight, and preferably 0.5-90% by weight, of the mixture, whereas carrier composition mixtures suitable for direct application or field application generally contemplate those in which the active compound is present in an amount substantially between about 0.0001-70%, preferably 0.005 – 10% by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001-95%, and preferably 0.005-95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50-100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20-100% by weight of the active compound.

In general the active compounds are applied in amounts of from 0.03-10 kg per hectare, preferably from 0.3 to 6 kg per hectare. It is, however, possible to employ higher or lower amounts and in some cases this may actually prove necessary.

Furthermore, the present invention contemplates methods of selectively killing, combating or controlling pests, e.g. fungi, which comprises applying to at least one of correspondingly (a) such fungi, and (b) the corresponding habitat thereof, i.e. the locus to be protected, e.g. to a growing crop, to an area where a crop is to be grown or to a domestic animal, a correspondingly combative or toxic amount, i.e. a fungicidally effective amount, of the particular active compound of the invention alone or together with a carrier vehicle as noted above. The instant formulations or compositions are applied in the usual manner, for instance, by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

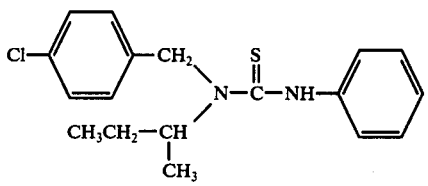 (1)

Process Variant (a)

20 g of N-(4-chlorobenzyl)-N-sec.-butylamine were dissolved in 500 ml of ether. To the resulting solution, a solution of 14 g of phenyl isothiocyanate in 50 ml of ether was added dropwise, under cooling and stirring. After the dropwise addition, the temperature of the solution was gradually raised, and the solution was then stirred at room temperature for about 10 hours. The crystals which had been formed were separated by filtration. After recrystallization with a solvent mixture of hexane and ethyl alcohol, 30 g of N-(4-chlorobenzyl)-N-sec.-butyl-N'-phenylthiourea were obtained. Yield: 91%. Melting point: 134°–134.5° C.

Process Variant (b)

19 g of aniline were dissolved in 300 ml of toluene. To the resulting solution, a solution of 28 g of N-(4-chlorobenzyl)-N-sec.-butyl-thiocarbamoyl chloride in 70 ml of toluene was added dropwise, under cooling and stirring. After the dropwise addition, the temperature of the solution was gradually raised, and then the solution was stirred at a temperature of 70°–80° C for about 5 hours. The solution was cooled to precipitate aniline hydrochloride, which was then separated by filtration. The toluene layer was washed with 100 ml of cold water and dried with anhydrous sodium sulfate. Then, the toluene was distilled off. The residue was subjected to recrystallization from a mixture of hexane and ethyl alcohol, whereby 23 g of N-(4-chlorobenzyl)- N-sec.-butyl-N'-phenylthiourea were obtained. Yield: 70%. Melting point: 134°–134.5° C.

It will be seen from this, that a excess of aniline may serve as the acid-binding agent in process variant (b).

EXAMPLE 2

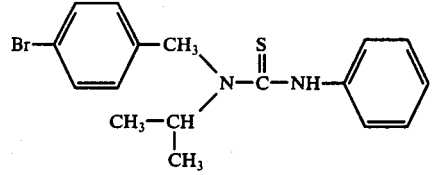 (2)

Following the procedure described in Example 1, process variant (a), 23 g of N-(4-bromobenzyl)-N-isopropylamine were reacted with 14 g of phenyl isothiocyanate. 32 g of N-(4-bromobenzyl)-N-isopropyl-N'-phenylthiourea were obtained. Yield: 88%. Melting point: 133.5°–134.5° C.

The following compounds were prepared according to methods analogous to process variant (a) described above in Example 1.

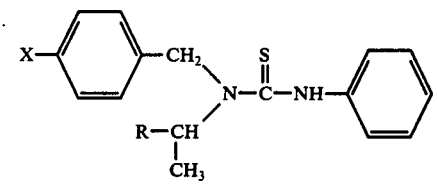 (I)

Table 1

| Compound No. | R | X | Melting point |
|---|---|---|---|
| 3 | C₂H₅ | Br | 133.5–134° C |
| 4 | CH₃ | Cl | 116–118° C |
| 5 | C₂H₅ | F | 143–144° C |

The following additional compounds can be so prepared:

Table 2

| Compound No. | R | X |
|---|---|---|
| 6 | C₃H₇-n | Cl |
| 7 | CH3 | I |
| 8 | C₃H₇-i | F |
| 9 | C₄H₉-n | Br |

EXAMPLE 3

50 Parts by weight of compound No. 1, 45 parts of a mixture of diatomaceous earth and kaolinite (1:5) and 5 parts of an emulsifier, Runnox (a polyoxyethylene alkylphenyl ether produced by Toho Kagaku Kogyo Co. Ltd.), were mixed together and ground into a wettable powder. This was diluted with water to an active-compound concentration of 0.05% before application by spraying.

EXAMPLE 4

30 Parts by weight of compound No. 3, 30 parts of xylene, 30 parts of Kawakasol (a mixture of high-boiling-point aromatic hydrocarbons, produced by Kawasaki Kasei Kogyo Co. Ltd) and 10 parts of Sorpol (a polyoxyethylene alkylaryl ether produced by Toho Kagaku Kogyo Co. Ltd.), were mixed and ground into an emulsion. This was diluted with water to an active compound concentration of 0.05% before being applied by spraying.

EXAMPLE 5

2 Parts by weight of compound No. 1 and 98 parts of a mixture of talc and clay (1:3) were mixed and ground into a dusting agent.

EXAMPLE 6

1.5 Parts by weight of compound No. 4, 0.5 part of isopropyl hydrogen phosphate (PAP) and 98 parts of a mixture of talc and clay (1:3) were mixed and ground into a dusting agent.

EXAMPLE 7

To a mixture of 10 parts by weight of compound No. 3, 10 parts of bentonite, 78 parts of a mixture of talc and clay (1:3) and 2 parts of a ligninsulfonic acid salt, there were added 25 parts of water. The whole was intimately mixed, finely cut by an extruding granulator, formed into granules of between 20 and 40 mesh size and dried at a temperature of 40°-50° C. The resulting granules were applied by scattering.

EXAMPLE 8

95 Parts by weight of clay granules having a size distribution of between 0.2 and 2 mm werecharged into a rotary mixer and evenly wetted by spraying them with 5 parts of compound No. 5 (which had been dissolved in an organic solvent) during the rotation. The granules were then dried at a temperature of 40°-50° C.

EXAMPLE 9

0.5 Part by weight of compound No. 2, 20 parts of Belsicol AR-50 (a mixture of high-boiling-point aromatic compounds and the like produced by Belsicol Co. Ltd.) and 79.5 parts of kerosene were mixed with stirring to form an oily preparation.

EXAMPLE 10

Rice Plant Sheath Blight Control Test (Pot Test)

| Preparation of fungicidal composition | |
|---|---|
| Active compound: | 50 parts by weight |
| Carrier: | 45 parts of a mixture (1:5) of diatomaceous earth and kaolin |
| Emulsifier: | 5 parts by weight of polyoxyethylene alkylphenyl ether |

The above-mentioned amounts of the active compound, carrier and emulsifier were mixed with one another to form a wettable powder which was diluted with water to the desired concentration.

Test procedure:

Rice plants (Kinmaze variety) were grown in Wagner pots (1/5000 Are) under paddy field conditions. When the rice plant was in the young-ear stage, a liquid preparation, which contained an active compound at a desired concentration, was applied thereto in an amount of 100 ml per three pots.

One day after the active compound had been applied, the plants were inoculated with the fungus *Pellicularia sasakii* (which had been grown in a barley medium for 10 days to form its sclerotia). The plants were kept in a greenhouse at a temperature of 28°-30° C and at a relative humidity of at least 95% to incubate the disease. After that, the degree of infection was evaluated, and the phytotoxicity of the active compound was checked. In this evaluation, the extent of the lesion portion spreading from the inoculation point (which was on the lower portion of the plant) was measured, and then the following calculation was made:

$$\text{Degree of infection (\%)} = \frac{3n_3 + 2n_2 + n_1 + n_0}{3N} \times 100$$

wherein
$N$ represents the total number of the plant stems observed,
$n_0$ represents the number of the stems which were not infected,
$n_1$ represents the number of stems which were infected over an area extending from the lower portion to the first leaf sheath portion,
$n_2$ represents the number of stems which were infected over an area extending from the lower portion to the second leaf sheath portion, and
$n_3$ represents the number of stems which were infected over an area extending from the lower portion to the third leaf sheath portion (or to a more distant portion).

The test results are shown in Table 3. The symbol "–", given in the column "Phytotoxicity" in this table means that no phytotoxicity was observed.

Table 3

| | Rice plant sheath blight control test | | |
|---|---|---|---|
| Active compound No. | Active compound conc. % | Degree of infection % | Phytotoxicity |
| 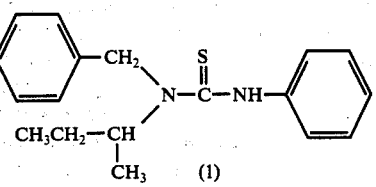 | 0.025 0.05 | 5.2 0 | — — |

Table 3-continued

Rice plant sheath blight control test

| Active compound No. | Active compound conc. % | Degree of infection % | Phytotoxicity |
| --- | --- | --- | --- |
| 4-Br-C6H4-CH2-N(CH(CH3)CH2CH3)-C(=S)-NH-C6H5 (3) | 0.025 | 9.7 | — |
| | 0.05 | 0 | — |
| 4-Cl-C6H4-CH2-N(CH(CH3)2)-C(=S)-NH-C6H5 (4) | 0.025 | 21.0 | — |
| | 0.05 | 9.5 | — |
| 4-F-C6H4-CH2-N(CH(CH3)CH2CH3)-C(=S)-NH-C6H5 (5) | 0.025 | 23.3 | — |
| | 0.05 | 11.5 | — |
| 4-Br-C6H4-CH2-N(CH(CH3)2)-C(=S)-NH-C6H5 (2) | 0.05 | 15.6 | — |
| (a): 3,4-Cl2-C6H3-CH2-N(CH3)-C(=S)-NH-C6H3-3,4-Cl2 (Japanese Appln. 29252/1969) | 0.05 | 84.3 | — |
| "Polyoxine" | 0.0045 | 25.3 | — |
| No treatment | — | 88.5 | |

EXAMPLE 11

Yound Seedling Damping-off Control Test (Greenhouse)

This biotest Example describes the treatment of soil with the active compounds to control the soil-borne infective fungus, *Pellicularia filamentosa*, which causes the damping-off of young seedlings of various crop plants.

Preparation of active compound:

To produce a suitable preparation of active compound, 3 parts by weight of active compound were mixed with 97 parts of talc to form a powder.

Test procedures:

*Pellicularia filamentosa*, which had been grown in a bran medium for 10 days, was inoculated into an upland field soil (clay loam) to form "an inoculated soil". Then the preparation of active compound mentioned above was introduced into the soil so that it contained the active compound at a desired concentration. In this treatment, a thorough mixing was carried out. The treated soil and a control sample of untreated soil were each placed in plastic boxes having an area of 27 cm × 18 cm and a depth of 9 cm. Into these boxes, seeds of cucumbers, egg plants and Japanese radish were sown in an amount of 50 grains per box. The boxes were placed in a greenhouse and maintained under ordinary plant growth conditions. At regular time intervals, the plants were observed to record the number of the seedlings which had been infected, and also to check the phytotoxicity of the active compound. Twenty-five days after the sowing, the total number of infected seedlings was recorded.

The test results are shown in Table 4. The symbol "-", shown in the column "Phytotoxicity" in the table, means that there was no phytotoxicity.

Table 4

| Active compound No. | Active compound concentration (ppm) | Cucumber Degree of infection (%) | Phyto-toxicity | Egg plant Degree of infection (%) | Phto-toxicity | Japanese radish Degree of infection (%) | Phyto-toxicity |
|---|---|---|---|---|---|---|---|
| (Compound 1): 4-Cl-C₆H₄-CH₂-N(CH(CH₃)CH₂CH₃)-C(=S)-NH-C₆H₅ | 25 / 50 | 4 / 0 | — / — | 0 / 0 | — / — | 3 / 0 | — / — |
| (Compound 3): 4-Br-C₆H₄-CH₂-N(CH(CH₃)CH₂CH₃)-C(=S)-NH-C₆H₅ | 25 / 50 | 12 / 2 | — / — | 7 / 0 | — / — | 6 / 3 | — / — |
| (Compound 4): 4-Cl-C₆H₄-CH₂-N(CH(CH₃)₂)-C(=S)-NH-C₆H₅ | 50 | 10 | — | 5 | — | 8 | — |
| (a): 3,4-Cl₂-C₆H₃-CH₂-N(CH₃)-C(=S)-NH-C₆H₃-3,4-Cl₂ (Japanese Appln. 29252/1969) | 50 | 100 | — | 100 | — | 100 | — |
| No treatment | — | 100 | — | 100 | — | 100 | — |

It will be appreciated that the instant specification and examples are set forth by way of illustration and not limitation, and that various modifications and changes may be made without departing from the spirit and scope of the present invention.

What is claimed is:

1. An N-(4-halobenzyl)-N-sec. alkyl-N'-phenylthiourea of the formula

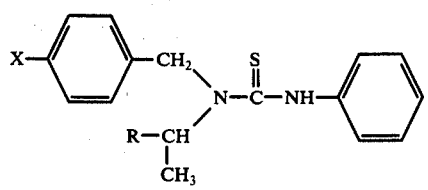

in which
R is a C₁–C₆ alkyl radical, and
X is a halogen atom.

2. A compound according to claim 1, in which R is a C₁–C₄ alkyl radical.

3. The compound according to claim 1, wherein such compound is N-(4-chlorobenzyl)-N-sec.-butyl-N'-phenylthiourea of the formula

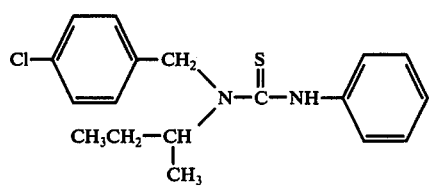

4. The compound according to claim 1, wherein such compound is N-(4-bromobenzyl)-N-isopropyl-N'-phenylthiourea of the formula 5. The compound according to claim 1, wherein such compound is N-(4-bromobenzyl)-N-sec.-butyl-N'-phenylthiourea of the formula

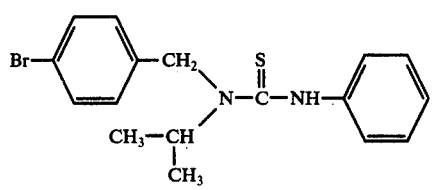

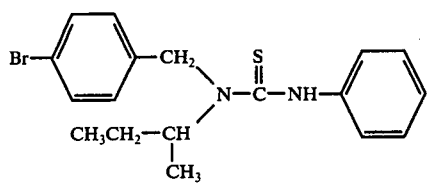

6. The compound according to claim 1, wherein such compound is N-(4-chlorobenzyl)-N-isopropyl-N'-phenylthiourea of the formula

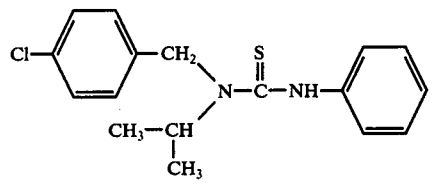

7. The compound according to claim 1, wherein such compound is N-(4-fluorobenzyl)-N-sec.-butyl-N'-phenylthiourea of the formula

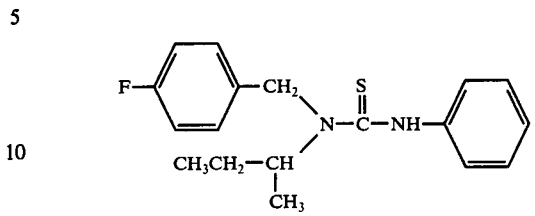

8. A fungicidal composition containing as the active ingredient a fungicidally effective amount of a compound according to claim 1 in admixture with a diluent.

9. A method of combating fungi which comprises applying to the fungi or a fungus habitat a fungicidally effective amount of a compound according to claim 1.

10. The method according to claim 9, in which said compound is N-(4-chlorobenzyl)-N-sec.-butyl-N'-phenylthiourea, N-(4-bromobenzyl)-N-isospropyl-N'-phenylthiourea, N-(4-bromobenzyl)-N-sec.-butyl-N'-phenylthiourea or N-(4-chlorobenzyl)-N-isopropyl-N'-phenylthiourea.

* * * * *